United States Patent [19]

Wokalek

[11] Patent Number: 5,076,265

[45] Date of Patent: Dec. 31, 1991

[54] HYDROGEL SHEET WOUND DRESSINGS

[75] Inventor: Heinrich Wokalek, Freiburg, Fed. Rep. of Germany

[73] Assignee: Ed Geistlich Sohne A.G. fur Chemische Industrie, Wolhusen, Switzerland

[21] Appl. No.: 399,486

[22] PCT Filed: Mar. 11, 1988

[86] PCT No.: PCT/GB88/00193

§ 371 Date: Nov. 1, 1989

§ 102(e) Date: Nov. 1, 1989

[87] PCT Pub. No.: WO88/06894

PCT Pub. Date: Sep. 22, 1988

[30] Foreign Application Priority Data

Mar. 13, 1987 [GB] United Kingdom ................ 8705985

[51] Int. Cl.$^5$ ...................... A61F 13/00; A61F 15/00; A61L 15/00
[52] U.S. Cl. .................................... 128/156; 604/304; 604/364; 424/443
[58] Field of Search ................ 128/156; 604/304, 307, 604/364, 368; 424/443, 445, 448

[56] References Cited

U.S. PATENT DOCUMENTS

| 4,341,207 | 7/1982 | Steer et al. ............................ 128/155 |
| 4,541,426 | 9/1985 | Webster ................................ 128/156 |
| 4,556,056 | 12/1985 | Fischer et al. . |
| 4,587,284 | 5/1986 | Luissi et al. ............................ 524/17 |
| 4,588,400 | 5/1986 | Ring et al. ............................. 128/156 |
| 4,655,758 | 4/1987 | Ring et al. . |

FOREIGN PATENT DOCUMENTS

| 0206830 | 12/1986 | European Pat. Off. . |
| 1594389 | 5/1978 | United Kingdom . |
| 2036042 | 6/1980 | United Kingdom . |
| 2131701 | 12/1983 | United Kingdom . |

Primary Examiner—Randall L. Green
Assistant Examiner—Paul Prebilic
Attorney, Agent, or Firm—Rothwell, Figg, Ernst & Kurz

[57] ABSTRACT

A hydrogel sheet for use as a wound dressing with capillaries permitting wound exudate to pass through the sheet while not permitting bacteria to infect the wound is disclosed. The total cross-sectional area of the capillaries represents 0.5 to 3.0 percent of the area of the sheet. The sheets do not stick to the wound surface and allow large quantities of wound exudate to be removed from the wound.

9 Claims, No Drawings

HYDROGEL SHEET WOUND DRESSINGS

The present invention relates to hydrogel dressings, their use and their manufacture.

Traditional wound dressings usually comprise a fabric or felt of absorptive material such as a gauze in direct contact with the wound. Such dressings are normally covered in order to avoid or reduce bacterial contamination but are not efficient in this respect. They have the general advantage of absorbing exudate from the wound but on the other hand, tend to stick to the wound surface, thus inhibiting healing. Furthermore, removal of the dressing is commonly painful where such sticking has taken place.

More recently, hydrogels have been proposed as wound dressings. The high water content of the gel is particularly compatible with the exposed surface of the wound and healing is significantly enhanced. There is in general no tendency to stick to the wound so that removal of the dressing is relatively painless.

A particular feature of such hydrogel dressings has been that they are impermeable to bacteria and thus serve to maintain the sterility of the healing surface, whereas fabric dressings, being porous, tend to permit bacterial invasion. This has been a significant factor in the promotion of hydrogel sheets for use as dressings.

In general, hydrogel dressings, even though moist, are able to absorb a moderate amount of exudate from the wound. However, where excessive production of wound exudate is encountered, the absorptive capacity of the hydrogel may be exceeded. It has been proposed to use hydrogel granules adhered to a non-porous backing in order to enhance absorption of exudate. In promotional literature on such products great emphasis has been laid on the impermeability of the backing and the resistance to bacterial invasion. However, there is some tendency for the granular hydrogel to stick to the wound surface and require removal, thus hindering healing.

We have now found that the above problems may be combated particularly satisfactorily by using a dressing comprising a hydrogel in sheet form with capillaries passing through the sheet. Excess exudate may then pass through the dressing and can be absorbed by a suitable absorptive dressing or compress placed over the hydrogel. If the size and numbers of such capillaries are suitably chosen, it is possible to deal with excess exudate while avoiding the problem of bacterial invasion found with traditional porous dressings.

The invention thus provides hydrogel sheets for use as wound dressings, said sheets being provided with capillaries which permit wound exudate to pass through the sheets while not permitting bacteria to infect the wound.

The capillaries are preferably of such diameter that the forces drawing liquid through the dressing from the wound are adequate. If the capillaries are too narrow, proteins, cells and other solids will block the flow of liquid, although it has been observed that the capillary forces are unusually high due to the particular surface properties of the hydrogel. If the capillaries are too wide, the capillary forces will be insufficient to draw liquid from the wound and may permit bacterial invasion.

Furthermore, the initial requirement of the dressing is to permit or enhance removal of suppurating liquid from the wound. While this process continues and there is a positive flow of liquid away from the wound, bacteria will not be able to invade in a contrary direction. However, as the flow of liquid subsides, chains of protein material and cells will build up in the capillaries so blocking them and preventing bacterial invasion. Eventually, a sheet of new tissue will develop which will completely block bacterial invasion. It will be appreciated that the relatively small area represented by the capillaries will not have any significant effect on the ease of removal of the dressing.

In general, the total cross-sectional area of the capillaries should represent 0.5 to 3.0% of the area of the hydrogel sheet, preferably 1 to 2%, e.g. about 1.5%. The capillaries may, for example be spaced 5 to 20 mm apart, conveniently in longitudinal and transverse rows; they will normally be of circular cross-section, having diameters in the range 0.5 to 3 mm, preferably 1–2.5 mm, e.g. about 2 mm.

The hydrogel sheets will generally be between 2 and 10 mm in thickness, preferably between 3 and 5 mm, e.g. about 3.5 mm. The lateral dimensions of the sheets may be adapted to the wound to be treated, e.g. by cutting.

The hydrogel sheets are preferably in accordance with the disclosure of GB-A-1594389 and may thus comprise a gelable polysaccharide and/or protein or polypeptide interspersed with a polymer of a hydrophilic acrylic acid or methacrylic acid derivative. However, instead of the acrylic or methacrylic acid derivative, other hydrophilic polymers may be used, for example polyvinylpyrrolidone. The hydrophilic acrylic or methacrylic acid derivative is preferably an amide, more preferably acrylamide, or an ester with an alkanol, optimally a polyol, especially preferably a $C_{1-6}$ alkanol such as methanol or ethanol. Conventional bi- or polyfunctional cross-linking agents such as N,N'-methylene-bis-acrylamide may be used to cross-link the polymer.

The gelable polysaccharide is preferably agarose or agar-agar while amongst gelable proteins and polypeptides, gelatine is preferred.

The water content of such a hydrogel can be very high, for example in the range 95 to 98% by weight, preferably about 97%. Thus, the solid matrix of the gel may constitute only 2 to 5% by weight of the gel, preferably about 3%.

In general, the most preferred hydrogels comprise (a) agar-agar together with (b) polyacrylamide cross-linked with about 2% by weight of N,N'-methylene bis-acrylamide, advantageously in the ratio range 1:3 to 1:4, preferably about 1:3.5. This gel, when fully swollen with water, contains about 96.5% by weight of water. A gel of this type is now commercially available from Geistlich Pharma of Wolhusen, Switzerland under the Registered Trade Mark Geliperm.

Hydrogel dressings according to the invention may be used in surgery in the preparation of the wound base for free skin transplantation; in the treatment of the donor site after the removal of split skin grafts in plastic surgery and for covering superficial operation wounds to prevent exposed bradytrophic tissue (tendons, periostium, bone or cartilage) from drying out. In dermatology, the hydrogel dressings may be used in the treatment of both fresh and chronic damage to the epithelium e.g. after dermal abrasion; to encourage granulation and the formation of cellular tissue in chronic ulcers, especially crural ulcers, decubitus sores etc; in the treatment of patients with polyvalent allergies when other forms of dressings and external applications are contra-indicated; and in the treatment of superficial thrombo-phlebitis in combination with external therapeutic measures used in such cases.

In general surgical debridement should be carried out to remove necrotic tissue prior to the application of the hydrogel sheet. Deep fissured wounds containing pockets of infected pus or necrotic tissue should be treated by appropriate therapeutic measures prior to the application of the sheet. Primarily strongly infected wounds should be treated with antimicrobial agents either prior to, or in combination with the hydrogel dressings.

The hydrogel dressings should be changed in accordance with individual clinical preference. Where the dressings are left in situ for more than 24 hours under a dry dressing, regular irrigation with appropriate aqueous solutions (e.g. saline) should be carried out to prevent dehydration. In instances where the hydrogel sheet has been allowed to dehydrate, rehydration should be carried out before removal.

A gauze dressing may be used to cover the hydrogel sheet and a compression bandage on top of it. This helps the patient keep mobile for instance in crural ulcer.

It should be noted that the hydrogel sheets according to the invention are generally permeable to salts, nutrients and antibiotics as well as proteins of higher molecular weight. However, since the hydrogel sheets are generally very pliable they can adapt themselves closely to the shape of the wound and promote coagulation, as is evident particularly in cases of dermal abrasion. A further favourable factor is the plane compression of the wound base which prevents the formation of wound oedema and results in an improvement in the circulation of the blood in the wound area. A fibrin-wall, rich in leucocytes forms between the hydrogel sheet and the surface of the wound, which may be interpreted as the body's own defensive barrier. Owing to this leucocyte-rich wall of fibrin which forms after the application of the hydrogel sheet, use of local antibiotics and other external applications is, in the case of chronic ulcers, as a rule superfluous, as these substances may, in fact, be found to inhibit epithelial proliferation.

The hydrogel sheets according to the invention may be prepared from unperforated sheet of the hydrogel material, which may be substantially as described in GB-A-1594389. Thus, the capillaries in the sheets may be provided by subsequent perforation.

However, on account of the very great pliancy of the hydrogel material, it is not normally sufficient simply to push a series of needles or thin rods through the sheets, since on removal of these, the holes tend to close without leaving significant capillaries in the material. It is generally necessary, therefore, to remove cores of hydrogel material from the sheets to provide the necessary capillaries, e.g. using hollow needles or syringes, which are conveniently connected to a vacuum line to assist removal of the material. The syringes will generally be slightly larger than the required capillaries, for example 0.5 to 5 mm, e.g. 2.5 mm.

Alternatively, it is possible to form the sheets in moulds provided with a series of upward projections such that on removal of the sheets from the mould, appropriate capillaries are formed.

The following example is given by way of illustration only:

EXAMPLE 20 g of agar-agar are suspended under agitation in 880 g of deionized water and heated to 95° C. until complete dissolution. 1 litre of a second aqueous solution containing 70 g of acrylamide and 1.84 g of N,N'-methylene-bis-acrylamide is prepared at ambient temperature and added to the first solution with thorough mixing. Under continued agitation, 2.2 g of N,N,N',N'-tetrakis-(2-hydroxypropyl)-ethylene diamine dissolved in 60 g of water and then 1.26 g of ammonium peroxidisulfate dissolved in 40 g of water are added.

The mixture is poured into flat moulds (26×12 mm) to a depth of 3 mm.

The mixture has a temperature between 50° C. and 55° C. and begins to polymerize immediately. After 10 minutes the gel point is reached. The batch is allowed to cool down overnight during which time polymerization is completed.

The gel is freed from soluble impurities by washing with pure flowing water for 24 hours. With this washing the gel swells to 135% of its original weight. Such sheet material is now commercially available under the name Geliperm from Geistlich Pharma of Wolhusen, Switzerland.

The sheets are then perforated with an array of 2.5 mm syringes connected to a vacuum line, to provide rows of 2 mm capillaries spaced at 15 mm intervals in both the longitudinal and lateral directions.

The perforated sheets are placed in plastic trays which are then heat sealed with clear plastic sheet. The sealed trays are then sterilised.

I claim:

1. A hydrogel sheet for use as a wound dressing, said sheet consisting essentially of a single hydrogel sheet provided with open capillaries which permit wound exudate to pass through the sheet while not permitting bacteria to infect the wound, wherein the total cross-sectional area of the open capillaries represents 0.5 to 3.0% of the area of the said sheet.

2. A hydrogel sheet as claimed in claim 1 wherein the capillaries are of circular cross-section with a diameter of 0.5 to 3 mm.

3. A hydrogel sheet as claimed in claim 1, said sheet having a uniform thickness of 2 to 10 mm.

4. A hydrogel sheet as claimed in claim 1 comprising a gel selected from the group consisting of gelable polysaccharides, proteins and polypeptides.

5. A hydrogel sheet as claimed in claim 4 wherein said gel is selected from the group consisting of agarose, agar-agar, and gelatin.

6. A hydrogel sheet as claimed in claim 5 wherein the gel comprises
   (a) agar-agar and
   (b) polyacrylamide cross-linked with about 2% by weight of N,N'-methylene-bis-acrylamide,
the ratio of (a) to (b) being in the range 1:3 to 1:4.

7. A hydrogel sheet as claimed in claim 1 having a water content in the range 95 to 98% by weight.

8. A method of treatment of a wound in the human or animal body comprising the application to said wound of a hydrogel sheet according to claim 1, whereby wound exudate is drawn from the wound through the dressing by forces within the capillaries of the said hydrogel sheet.

9. A method as claimed in claim 8 further comprising the step of irrigating the dressing with an aqueous solution after application of the dressing to said wound.

* * * * *